United States Patent [19]

Fischer et al.

[11] 3,954,827

[45] May 4, 1976

[54] SUBSTITUTED O-[AMINOSULFONYL]-GLYCOLIC ANILIDES

[75] Inventors: Adolf Fischer, Mutterstadt; Gerhard Hamprecht, Mannheim; Dietrich Mangold, Neckargemuena; Wolfgang Rohr, Mannheim, all of Germany

[73] Assignee: BASF Aktiengesellschaft, Ludwigshafen (Rhine), Germany

[22] Filed: Sept. 3, 1974

[21] Appl. No.: 502,741

Related U.S. Application Data

[62] Division of Ser. No. 321,548, Jan. 5, 1973, Pat. No. 3,870,740.

[52] U.S. Cl............................................ 260/456 A
[51] Int. Cl.$^2$........................................ C07C 143/68
[58] Field of Search................................ 260/456 A

[56] References Cited
UNITED STATES PATENTS 3,536,721   10/1970   Soong et al.................... 260/456 A

*Primary Examiner*—James O. Thomas, Jr.
*Assistant Examiner*—Nicky Chan
*Attorney, Agent, or Firm*—Johnston, Keil, Thompson & Shurtleff

[57] ABSTRACT

New and valuable substituted O-[aminosulfonyl]-glycolic anilides and a process for controlling the growth of unwanted plants with these compounds.

3 Claims, No Drawings

SUBSTITUTED O-[AMINOSULFONYL]-GLYCOLIC ANILIDES

This is a division of application Ser. No. 321,548 filed Jan. 5, 1973 now U.S. Pat. No. 3,870,740.

The present invention relates to new and valuable substituted O-[aminosulfonyl]-glycolic anilides, their preparation and use as herbicides.

It is known to use chloroacetic acid-N-isopropylanilide as a herbicide. However, its biological action is only moderate.

We have now found that substituted O-[aminosulfonyl]-glycolic anilides of the formula

where $R^1$ denotes hydrogen, alkyl, haloalkyl or cycloalkyl, $R^2$ denotes phenyl and $R^3$ denotes alkyl, alkenyl, alkynyl, cycloalkyl or benzyl, have a good herbicidal action.

$R^1$ may be, inter alia, methyl, ethyl, propyl, isopropyl, butyl, isobutyl, sec-butyl, pentyl, cyclopentyl, hexyl, cyclohexyl 2-chloroethyl.

$R^3$ may be, inter alia, methyl, ethyl, propyl, isopropyl, n-butyl, isobutyl, sec-butyl, tert-butyl, pentyl, cyclopentyl, hexyl, cyclohexyl, allyl, butenyl, pentenyl, hexenyl, propargyl, butynyl, pentynyl, hexynyl, benzyl.

The herbicidal action of the new compounds is particularly in evidence on the following weeds:

| | |
|---|---|
| Alopecurus myosuroides | slender foxtail |
| Amaranthus spp. | amaranth species |
| Avena fatua | wild oat |
| Bromus spp. | brome species |
| Chenopodium spp. | goosefoot species |
| Dactylis glomerata | orchardgrass |
| Digitaria sanguinalis | large crabgrass |
| Echinochloa crus-galli | barnyardgrass |
| Eleusine indica | goosegrass |
| Galium aparine | catchweed bedstraw |
| Lamium spp. | deadnettle species |
| Lolium spp. | ryegrass species |
| Matricaria chamomilla | chamomile |
| Panicium spp. | panicum spp. |
| Poa spp. | bluegrass species |
| Setaria spp. | foxtail species |
| Sinapis arvensis | wild mustard | without causing damage to the crop plants:

| | |
|---|---|
| Allium cepa | onions |
| Beta vulgaris | beet |
| Brassica spp. | cabbage species |
| Cucumis sativus | cucumbers |
| Daucus carota | carrots |
| Gossypium hirsutum | cotton |
| Helianthus annuus | sunflower |
| Hordeum vulgare | barley |
| Lactuca spp. | lettuce species |
| Linum usitatissimum | flax |
| Medicago sativa | alfalfa |
| Oryza sativa | rice |
| Petroselinum sativum | parsley |
| Pisum sativum | peas |
| Phaseolus spp. | beans |
| Secale cereale | rye |
| Soja hispida (Glycine max.) | soybeans |
| Solanum tuberosum | potatoes |
| Spinacia oleracea | spinach |
| Sorghum bicolor | sorghum |
| Triticum aestivum | wheat |
| Trifolium spp. | clover |
| Zea mays | Indian corn |

Application rates are from 0.2 to 5 kg of active ingredient per hectare; the compounds may be applied before sowing, or before or after emergence of the plants.

The compounds of the invention may be prepared by reacting a substituted glycolic anilide with a substituted aminolsulfonyl chloride in the presence of an acid acceptor, e.g., triethylamine and pyridine.

EXAMPLE 1

O-[isopropylaminosulfonyl]-glycolic acid-N-butyn-1-yl-3-anilide

At 0° to 5°C and while stirring, a solution of 333 parts by weight of isopropylaminosulfonyl chloride in 80 parts by weight of dichloromethane was added to a solution of 35.5 parts by weight of glycolic acid-N-butyn-1-yl-3-anilide and 21.4 parts by weight of triethylamine in 600 parts by weight of dichloromethane. After 2 hours the reaction mixture was successively washed with dilute hydrochloric acid, water, sodium bicarbonate solution, and again with water, and then dried with magnesium sulfate. The crude product, melting at 99° to 105°C, was obtained from the organic phase upon concentration in vacuo. The pure compound melting at 108° to 110°C may be obtained by recrystallization from benzene.

The compound has the following structural formula:

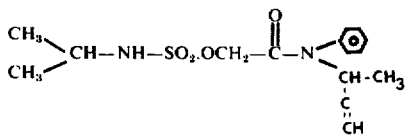

The compounds listed below may be obtained analogously:

| $R^1$ | $R^3$ | m.p.(°C) |
|---|---|---|
| H | $CH_3$ | 119 to 121 |
| $CH_3$ | $CH_3$ | 87 to 88 |
| $C_2H_5$ | $CH_3$ | 84 to 86 |
| n-$C_3H_7$ | $CH_3$ | |
| i-$C_3H_7$ | $CH_3$ | 134 to 135 |
| n-$C_4H_9$ | $CH_3$ | |
| i-$C_4H_9$ | $CH_3$ | |
| sec-$C_4H_9$ | $CH_3$ | |
| $CH_2ClCH_2$ | $CH_3$ | |
| $C_6H_{11}$ | $CH_3$ | |
| H | $C_2H_5$ | |
| $CH_3$ | $C_2H_5$ | |
| $C_2H_5$ | $C_2H_5$ | 60 to 62 |
| n-$C_3H_7$ | $C_2H_5$ | |
| i-$C_3H_7$ | $C_2H_5$ | 76 to 77 |
| n-$C_4H_9$ | $C_2H_5$ | |
| sec-$C_4H_9$ | $C_2H_5$ | |
| $CH_2ClCH_2$ | $C_2H_5$ | |
| $C_6H_{11}$ | $C_2H_5$ | |
| H | n-$C_3H_7$ | |
| $CH_3$ | n-$C_3H_7$ | 61 to 63 |
| $C_2H_5$ | n-$C_3H_7$ | |
| n-$C_3H_7$ | n-$C_3H_7$ | |
| i-$C_3H_7$ | n-$C_3H_7$ | 78 to 79 |
| n-$C_4H_9$ | n-$C_3H_7$ | |
| i-$C_4H_9$ | n-$C_3H_7$ | |
| sec-$C_4H_9$ | n-$C_3H_7$ | |
| $CH_2ClCH_2$ | n-$C_3H_7$ | |
| $C_6H_{11}$ | n-$C_3H_7$ | |
| H | i-$C_3H_7$ | |
| $CH_3$ | i-$C_3H_7$ | |
| $C_2H_5$ | i-$C_3H_7$ | |
| n-$C_3H_7$ | i-$C_3H_7$ | |
| i-$C_3H_7$ | i-$C_3H_7$ | |
| n-$C_4H_9$ | i-$C_3H_7$ | |

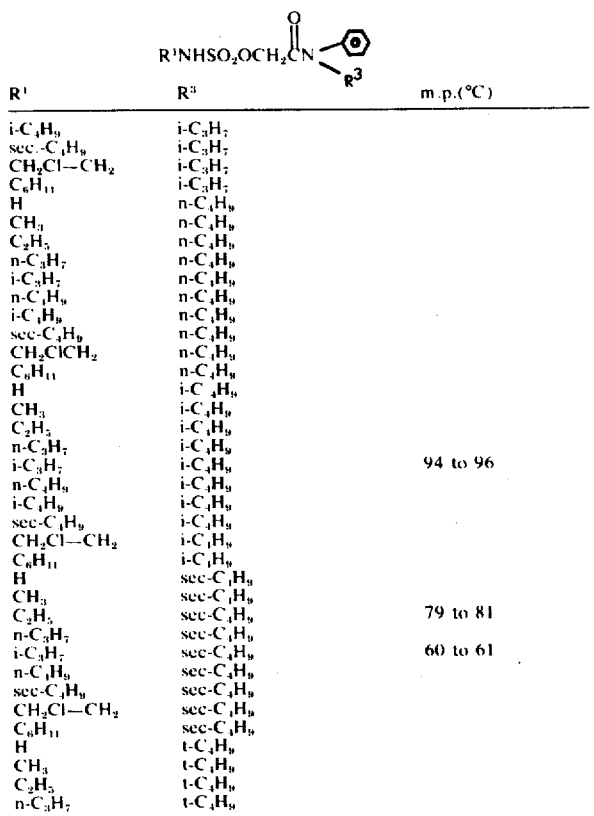

| $R^1$ | $R^3$ | m.p.(°C) |
|---|---|---|
| i-C₄H₉ | i-C₃H₇ | |
| sec-C₄H₉ | i-C₃H₇ | |
| CH₂Cl—CH₂ | i-C₃H₇ | |
| C₆H₁₁ | i-C₃H₇ | |
| H | n-C₄H₉ | |
| CH₃ | n-C₄H₉ | |
| C₂H₅ | n-C₄H₉ | |
| n-C₃H₇ | n-C₄H₉ | |
| i-C₃H₇ | n-C₄H₉ | |
| n-C₄H₉ | n-C₄H₉ | |
| i-C₄H₉ | n-C₄H₉ | |
| sec-C₄H₉ | n-C₄H₉ | |
| CH₂ClCH₂ | n-C₄H₉ | |
| C₆H₁₁ | n-C₄H₉ | |
| H | i-C₄H₉ | |
| CH₃ | i-C₄H₉ | |
| C₂H₅ | i-C₄H₉ | |
| n-C₃H₇ | i-C₄H₉ | |
| i-C₃H₇ | i-C₄H₉ | 94 to 96 |
| n-C₄H₉ | i-C₄H₉ | |
| i-C₄H₉ | i-C₄H₉ | |
| sec-C₄H₉ | i-C₄H₉ | |
| CH₂Cl—CH₂ | i-C₄H₉ | |
| C₆H₁₁ | i-C₄H₉ | |
| H | sec-C₄H₉ | |
| CH₃ | sec-C₄H₉ | |
| C₂H₅ | sec-C₄H₉ | 79 to 81 |
| n-C₃H₇ | sec-C₄H₉ | |
| i-C₃H₇ | sec-C₄H₉ | 60 to 61 |
| n-C₄H₉ | sec-C₄H₉ | |
| sec-C₄H₉ | sec-C₄H₉ | |
| CH₂Cl—CH₂ | sec-C₄H₉ | |
| C₆H₁₁ | sec-C₄H₉ | |
| H | t-C₄H₉ | |
| CH₃ | t-C₄H₉ | |
| C₂H₅ | t-C₄H₉ | |
| n-C₃H₇ | t-C₄H₉ | |
| i-C₃H₇ | t-C₄H₉ | |
| n-C₄H₉ | t-C₄H₉ | |
| sec-C₄H₉ | t-C₄H₉ | |
| CH₂Cl—CH₂ | t-C₄H₉ | 116 to 118 |
| C₆H₁₁ | t-C₄H₉ | |
| H | allyl | |
| CH₃ | allyl | |
| C₂H₅ | allyl | |
| n-C₃H₇ | allyl | |
| i-C₃H₇ | allyl | |
| n-C₄H₉ | allyl | |
| sec-C₄H₉ | allyl | |
| CH₂Cl—CH₂ | allyl | |
| C₆H₁₁ | allyl | |
| H | propargyl | |
| CH₃ | propargyl | |
| C₂H₅ | propargyl | |
| n-C₃H₇ | propargyl | |
| i-C₃H₇ | propargyl | 99 to 101 |
| n-C₄H₉ | propargyl | |
| sec-C₄H₉ | propargyl | |
| CH₂Cl—CH₂ | propargyl | |
| C₆H₁₁ | propargyl | |
| H | butyn-1-yl-3 | 145 to 147 |
| CH₃ | butyn-1-yl-3 | 118 to 120 |
| C₂H₅ | butyn-1-yl-3 | 134 to 136 |
| n-C₃H₇ | butyn-1-yl-3 | 74 to 77 |
| i-C₃H₇ | butyn-1-yl-3 | 108 to 110 |
| n-C₄H₉ | butyn-1-yl-3 | |
| sec-C₄H₉ | butyn-1-yl-3 | 66 to 67 |
| CH₂Cl—CH₂ | butyn-1-yl-3 | |

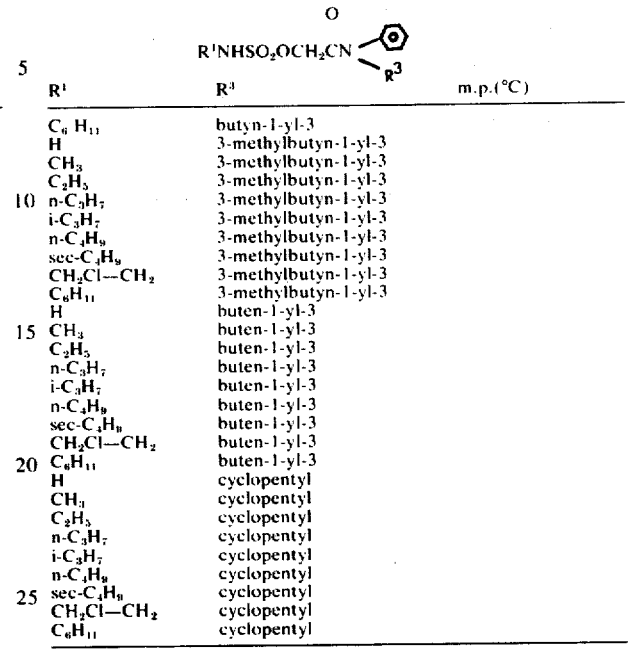

| $R^1$ | $R^3$ | m.p.(°C) |
|---|---|---|
| C₆H₁₁ | butyn-1-yl-3 | |
| H | 3-methylbutyn-1-yl-3 | |
| CH₃ | 3-methylbutyn-1-yl-3 | |
| C₂H₅ | 3-methylbutyn-1-yl-3 | |
| n-C₃H₇ | 3-methylbutyn-1-yl-3 | |
| i-C₃H₇ | 3-methylbutyn-1-yl-3 | |
| n-C₄H₉ | 3-methylbutyn-1-yl-3 | |
| sec-C₄H₉ | 3-methylbutyn-1-yl-3 | |
| CH₂Cl—CH₂ | 3-methylbutyn-1-yl-3 | |
| C₆H₁₁ | 3-methylbutyn-1-yl-3 | |
| H | buten-1-yl-3 | |
| CH₃ | buten-1-yl-3 | |
| C₂H₅ | buten-1-yl-3 | |
| n-C₃H₇ | buten-1-yl-3 | |
| i-C₃H₇ | buten-1-yl-3 | |
| n-C₄H₉ | buten-1-yl-3 | |
| sec-C₄H₉ | buten-1-yl-3 | |
| CH₂Cl—CH₂ | buten-1-yl-3 | |
| C₆H₁₁ | buten-1-yl-3 | |
| H | cyclopentyl | |
| CH₃ | cyclopentyl | |
| C₂H₅ | cyclopentyl | |
| n-C₃H₇ | cyclopentyl | |
| i-C₃H₇ | cyclopentyl | |
| n-C₄H₉ | cyclopentyl | |
| sec-C₄H₉ | cyclopentyl | |
| CH₂Cl—CH₂ | cyclopentyl | |
| C₆H₁₁ | cyclopentyl | |

The substituted glycolic anilides used as starting materials may be prepared by known methods. The following equations illustrate a possible route, $R^2$ and $R^3$ have the meanings given above:

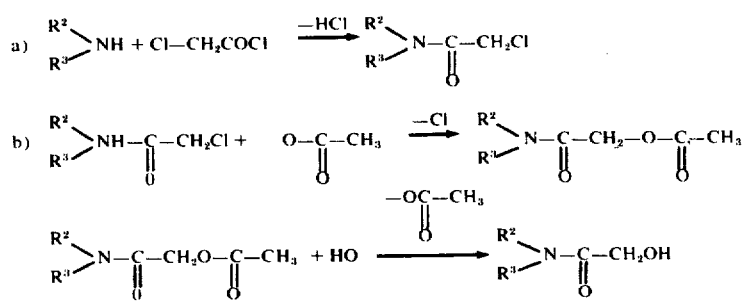

Glycolic acid-N-butyn-1-yl-3-anilide

264 Parts by weight of chloroacetic acid-N-butyn-1-yl-3-anilide (obtained from chloroacetyl chloride and N-butyn-1-yl-3-aniline) and 660 parts by weight of potassium acetate were boiled under reflux for 20 hours in 2,400 parts by weight of 1.5 molar acetic acid. After cooling, the O-acetylglycolic acid-N-butyn-1-yl-3-anilide which had formed was suction filtered and reacted as a crude product (m.p. 83° to 87°C). The pure compound (m.p. 95° to 96°C) is obtained by recrystallization from cyclohexane.

77 Parts by weight of crude O-acetylglycolic acid-N-butyn-1-yl-3-anilide was dissolved in a solution of 31 parts by weight of potassium hydroxide in 890 parts by weight of methanol and left to stand at room temperature for 16 hours. The reaction solution was then concentrated to roughly 150 ccm. Upon neutralization of the residue with dilute hydrochloric acid crystals of crude glycolic acid-N-butyn-1-yl-3-anilide separated out; m.p.: 65° to 67°C.

This crude product was purified by recrystallization from benzene/ligroin; m.p. 74° to 76°C.

The following compounds were obtained analogously: glycolic acid-N-isopropylanilide, m.p. 59° to 60°C glycolic acid-N-isobutylanilide, m.p. 53° to 54°C glyolic acid-N-tert-butylanilide, m.p. 55° to 56°C.

Glycolic anilides are obtained in the same manner by reacting, in accordance with the scheme shown below, N-alkylanilines with 1,3-dioxolane-2,4-dione (*J. Chem. Soc.*, 1357, 1951). $R^2$ and $R^3$ have the meanings given above.

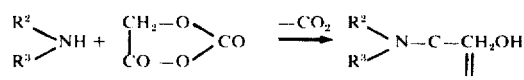

Glycolic acid-N-methylanilide

A solution of 10.7 parts by weight of N-methylaniline in 20 parts by weight of tetrahydrofuran has added to it, at 10° to 15°C and with stirring, a solution of 10.2 parts by weight of 1,3-dioxolane-2,4-dione in 20 parts by weight of tetrahydrofuran. The reaction mixture was then stirred at room temperature until no more carbon dioxide evolved, and subsequently concentrated to dryness in vacuo. The crude product obtained melts at 48° to 50°C; the analytically pure compound is obtained by recrystallization from ether; m.p.: 50° to 52°C.

The following compounds were obtained analogously:

glycolic acid-N-ethylanilide, m.p. 39° to 41°C
glycolic acid-N-n-propylanilide, m.p. 68° to 69°C
glycolic acid-N-propargylanilide, m.p. 69° to 71°C
glycolic acid-N-3-methylbutyn-1-yl-3-anilide
glycolic acid-N-allylanilide
glycolic acid-N-buten-1-yl-3-anilide
glycolic acid-N-3-methylbuetn-1-yl-3-anilide
glycolic acid-N-cyclohexylanilide
glycolic acid-N-cyclopentylanilide
glycolic acid-N-benzylanilide.

The agents according to the invention may be used as solutions, emulsions, suspensions or dusts. The form of application depends entirely on the purpose for which the agents are being used; in any case it should ensure a fine distribution of the active ingredient.

For the preparation of solutions to be sprayed direct, hydrocarbons having boiling points higher than 150°C, e.g. tetrahydronaphthalene or alkylated naphthalenes, or organic liquids having boiling points higher than 150°C and having one or more than one functional group, e.g. the keto group, the ether group, the ester group or the amide group, this group or these groups being attached as substituent(s) to a hydrocarbon chain or being a component of a heterocyclic ring, may be used as spray liquids.

Aqueous formulations may be prepared from emulsion concentrates, pastes or wettable powders by adding water. To prepare emulsions the ingredients as such or dissolved in a solvent may be homogenized in water or organic solvents by means of wetting or dispersing agents, e.g., polyethylene oxide adducts. Concentrates which are suitable for dilution with water may be prepared from active ingredient, emulsifying or dispersing agent and possibly solvent.

Dusts may be prepared by mixing or grinding the active ingredients with a solid carrier, e.g., kieselguhr, talc, clay or fertilizers.

Granules may be prepared by applying the active ingredients to solid carriers of various particle sizes.

Adherents, oils and other herbicidal active ingredients may also be added.

EXAMPLE 2

In the greenhouse, loamy sandy soil was filled into pots and sown with *Zea mays*, *Soja hispida*, *Gossypium hirsutum*, *Beta vulgaris*, *Echinochloa crus-galli*, *Setaria spp.*, *Poa trivialis*, *Bromus tectorum* and *Alopecurus myosuroides*. The soil prepared in this manner was then treated with 2 kg per hectare of O-(isopropylaminosulfonyl)-glycolic acid-N-butyn-1-yl-3-anilide (I) and, for comparison, with 20 kg per hectare of chloroacetic acid-N-isopropylanilide (II), each active ingredient being dispersed in 500 liters of water per hectare.

After 4 to 5 weeks it was ascertained that active ingredient I had the same good crop plant compatibility as II, combined with a stronger herbicidal action.

The results of this experiment are given below:

| Active ingredient | I | II |
|---|---|---|
| Zea mays | 0 | 0 |
| Soja hispida | 0 | 0 |
| Gossypium hirsutum | 0 | 0 |
| Beta vulgaris | 0 | 0 |
| Echinochloa crus-galli | 95 | 70 |
| Setaria spp. | 95 | 70 |
| Poa trivialis | 95 | 40 |
| Bromus tectorum | 95 | 40 |
| Alopecurus myosuroides | 90 | 50 |

0 = no damage
100 = complete destruction

EXAMPLE 3

On an agricultural plot the plants *Zea mays*, *Gossypium hirsutum*, *Soja hispida*, *Beta vulgaris*, *Echinochloa crus-galli*, *Digitaria sanguinalis*, *Panicum virgatum*, *Eleusine indica* and *Poa anna* were treated at a growth height of 2 to 14 cm with 2 kg per hectare of I and 2 kg per hectare of II, each active ingredient being emulsified in 500 liters of water per hectare.

After 3 to 4 weeks it was ascertained that active ingredient I had not only better crop plant compatibility than II, but also a stronger herbicidal action.

The results of this experiment are given below:

| Active ingredient | I | II |
|---|---|---|
| Zea mays | 0 | 0 |
| Gossypium hirsutum | 0 | 15 |
| Soja hispida | 5 | 15 |
| Beta vulgaris | 0 | 10 |
| Echinochloa crus-galli | 80 | 60 |
| Digitaria sanguinalis | 90 | 40 |
| Panicum virgatum | 90 | 40 |
| Eleusine indica | 90 | 30 |
| Poa annua | 80 | 15 |

0 = no damage
100 = complete destruction

The action of the following compounds corresponds to that of I above:

O-(isopropylaminosulfonyl)-glycolic acid-N-methylanilide
O-(isopropylaminosulfonyl)-glycolic acid-N-isobutylanilide O-(ethylaminosulfonyl)-glycolic acid-N-butyn-1-yl-3-anilide O-(isopropylaminosulfonyl)-blycolic acid-N-sec-butylanilide

EXAMPLE 4

90 Parts by weight of compound I is mixed with 10 parts by weight of N-methyl-α-pyrrolidone. A mixture is obtained which is suitable for application in the form of very fine drops.

EXAMPLE 5

20 Parts by weight of compound I is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution 100,000 100,000 parts by weight of water and uniformly distributing it therein, an aqueous dispersion is obtained containing 0.02% by weight of the active ingredient.

EXAMPLE 6

20 Parts by weight of compound I is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 7

20 Parts by weight of compound I is dissolved in a mixture consisting of 25 parts by weight of cyclohexanol, 65 parts by weight of a mineral oil fraction having a boiling point between 210°0 280°C, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 8

20 Parts by weight of compound I is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 9

3 Parts by weight of compound I is intimately mixed with 97 parts by weight of particulate kaolin. A dust is obtained containing 3% by weight of the active ingredient.

EXAMPLE 10

30 Parts by weight of compound I is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 11

Loamy sandy soil was filled into pots and sown with *Soja hispida, Gossypium hirsutum, Beta vulgaris, Brassica napus, Helianthus annuus, Pisum sativum, Allium cepa, Spinacia oleracea, Echinochloa crus-galli, Digitaria sanguinalis, Setaria faberii, Poa annua, Lolium multiflorum, Eleusine indica and Matricaria chamomilla.* The soil prepared in this manner was immediately treated with 20 kg per hectare of each of the following active ingredients:

I O-(isopropylaminosulfonyl)-glycolic acid-N-butyn-1-yl-3-anilide
III O-(propylaminosulfonyl)-glycolic acid-N-butyn-1-yl13-anilide
IV O-(isopropylaminosulfonyl)-glycolic acid-N-buten-1-yl-3-anilide
V O-(isopropylaminosulfonyl)-glycolic acid-N-methylanilide
VI O-(methylaminosulfonyl)-glycolic acid-N-butyn-1-yl-3-anilide
VII O-(isopropylaminosulfonyl)-glycolic acid-N-ethylanilide
VIII O-(ethylaminosulfonyl)-glycolic acid-N-ethylanilide After 3 weeks it was ascertained that the active ingredients exhibited good crop plant compatibility combined with an excellent herbicidal action.

The results are given below:

| Active ingredient | I | III | IV | V | VI | VII | VIII |
|---|---|---|---|---|---|---|---|
| Crop plants: | | | | | | | |
| Soja hispida | 0 | 5 | 0 | 0 | 0 | 0 | 0 |
| Gossypium hirsutum | 0 | 0 | 0 | 0 | 0 | 0 | 0 |
| Beta vulgaris | 0 | 0 | 0 | 0 | 0 | 0 | 0 |
| Brassica napus | 0 | 0 | 0 | 0 | 0 | 0 | 0 |
| Helianthus annuus | 0 | 0 | 0 | 0 | 0 | 0 | 0 |
| Allium cepa | 0 | 0 | 0 | 0 | 0 | 0 | 0 |
| Spinacia oleracea | 0 | 0 | 0 | 0 | 0 | 0 | 0 |
| Pisum sativum | 0 | 0 | 0 | 0 | 0 | 0 | 0 |
| Unwanted plants: | | | | | | | |
| Echinochloa crus-galli | 95 | 100 | 95 | 95 | 100 | 100 | 95 |
| Digitaria sanguinalis | 95 | 100 | 95 | 90 | 100 | 95 | 90 |
| Setaria faberii | 95 | 100 | 95 | 90 | 100 | 95 | 95 |
| Poa annua | 100 | 100 | 100 | 100 | 100 | 100 | 95 |
| Lolium multiflorum | 100 | 100 | 95 | 95 | 100 | 100 | 95 |
| Eleusine indica | 100 | 100 | 95 | 90 | 100 | 95 | 90 |

| Active ingredient | I | III | IV | V | VI | VII | VIII |
|---|---|---|---|---|---|---|---|
| Matricaria chamomilla | 80 | 90 | 80 | 80 | 90 | 80 | 75 |

0 = no damage
100 = complete destruction

EXAMPLE 12

In the greenhouse, the plants Soja hispida, Beta vulgaris, Gossypium hirsutum, Oryza sativa, Triticum aestivum, Zea mays, Alopecurus myosuroides, Lolium multiflorum, Setaria faberii, Eleusine indica, Echinochloa crus-galli, Chenopodium album and Matricaria chamomilla were treated at a growth height of 2 to 16 cm with 1 kg per hectare of each of the following active ingredients I O-(isopropylaminosulfonyl)-glycolic acid-N-butyn-1-yl-3-anilide
III O-(propylaminosulfonyl)-glycolic acid-N-butyn-1-yl-3-anilide
IV O-(isopropylaminosulfonyl)-glycolic acid-N-buten-1-yl-3-anilide
V O-(isopropylaminosulfonyl)-glycolic acid-N-methylanilide
VI O-(methylaminosulfonyl)-glycolic acid-N-butyn-1-yl-3-anilide
VII O-(isopropylaminosulfonyl)-glycolic acid-N-ethyl-anilide
VIII O-(ethylaminosulfonyl)-glycolic acid-N-ethylanilide.

After 3 weeks it was ascertained that the active ingredients exhibited favorable crop plant compatibility combined with a good herbicidal action.

The results are given below:

| Active ingredient | I | III | IV | V | VI | VII | VIII |
|---|---|---|---|---|---|---|---|
| Crop plants: | | | | | | | |
| Soja hispida | 0 | 0 | 0 | 0 | 0 | 5 | 0 |
| Beta vulgaris | 0 | 0 | 0 | 0 | 0 | 0 | 0 |
| Gossypium hirsutum | 0 | 0 | 0 | 0 | 0 | 0 | 0 |
| Oryza sativa | 10 | 5 | 5 | 15 | 5 | 20 | 5 |
| Triticum aestivum | 10 | 5 | 5 | 5 | 5 | 10 | 5 |
| Zea mays | 0 | 0 | 0 | 0 | 0 | 5 | 0 |
| Unwanted plants: | | | | | | | |
| Alopecurus myosuroides | 90 | 95 | 85 | 80 | 90 | 95 | 90 |
| Lolium multiflorum | 90 | 95 | 80 | 80 | 85 | 90 | 90 |
| Setaria faberii | 95 | 100 | 90 | 90 | 90 | 95 | 95 |
| Eleusine indica | 85 | 95 | 90 | 80 | 85 | 90 | 90 |
| Echinochloa crus-galli | 75 | 95 | 90 | 90 | 80 | 80 | 85 |
| Chenopodium album | 80 | 90 | 70 | 70 | 70 | 80 | 75 |
| Matricaria chamomilla | 80 | 90 | 75 | 75 | 70 | 80 | 80 |

0 = no damage
100 = complete destruction

The action of the following compounds corresponds to that of the compounds examined in Examples 11 and 12:

O-(aminosulfonyl)-glycolic acid-N-butyn-1-yl-3-anilide
O-(isopropylaminosulfonyl)-glycolic acid-N-tert-butylanilide
O-(methylaminosulfonyl)-glycolic acid-N-methylanilide
O-(ethylaminosulfonyl)-glycolic acid-N-methylanilide
O-(methylaminosulfonyl)-glycolic acid-N-n-propylanilide
O-(isopropylaminosulfonyl)-glycolic acid-N-n-propylanilide
O-(ethylaminosulfonyl)-glycolic acid-N-sec-butylanilide
O-(isopropylaminosulfonyl)-glycolic acid-N-ethylanilide
O-(isopropylaminosulfonyl)-glycolic acid-N-propargylanilide
O-(pentylaminosulfonyl)-glycolic acid-N-butyn-1-yl-3-anilide
O-(aminosulfonyl)-glycolic acid-N-methylanilide

We claim:

1. A substituted O-(aminosulfonyl)-glycolic glycolic anilide of the formula

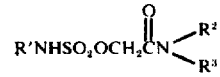

where R' denotes cyclopentyl or cyclohexyl, R² denotes phenyl, and R³ denotes alkyl of 1 to 6 carbon atoms.

2. The compound of claim 1, which is: O-(cyclohexylaminosulfonyl)-glycolic acid-N-isopropylanilide.

3. The compound of claim 1, which is: O-(cyclohexylaminosulfonyl)-glycolic acid-N-tert-butylanilide.

* * * * *